US008892197B2

(12) United States Patent
Ujhelyi et al.

(10) Patent No.: US 8,892,197 B2
(45) Date of Patent: Nov. 18, 2014

(54) METHOD AND APPARATUS TO CONTROL CONDUCTION THROUGH THE HEART TO TREAT CARDIAC CONDITIONS

(75) Inventors: Michael R. Ujhelyi, Maple Grove, MN (US); Daniel C. Sigg, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 1986 days.

(21) Appl. No.: 11/192,884

(22) Filed: Jul. 29, 2005

(65) Prior Publication Data

US 2007/0027394 A1  Feb. 1, 2007

(51) Int. Cl.
| | |
|---|---|
| A61B 5/04 | (2006.01) |
| A61M 31/00 | (2006.01) |
| A61M 5/142 | (2006.01) |
| A61N 1/05 | (2006.01) |
| A61M 5/172 | (2006.01) |
| A61N 1/365 | (2006.01) |

(52) U.S. Cl.
CPC ....... *A61M 5/14276* (2013.01); *A61M 2230/63* (2013.01); *A61M 2210/125* (2013.01); *A61M 2230/04* (2013.01); *A61M 5/1723* (2013.01); *A61N 1/0575* (2013.01); *A61N 1/365* (2013.01)
USPC ................................ 600/518; 604/66; 604/67

(58) Field of Classification Search
USPC ............... 607/9, 120; 600/508, 518, 509, 513
See application file for complete search history.

(56) References Cited

U.S. PATENT DOCUMENTS

| | | | |
|---|---|---|---|
| 21,091 A | 8/1858 | Stevens | |
| 3,692,027 A | 9/1972 | Ellinwood, Jr. | |
| 4,003,379 A | 1/1977 | Ellinwood, Jr. | |
| 4,146,029 A | 3/1979 | Ellinwood, Jr. | |
| 4,360,031 A | 11/1982 | White | |
| 5,713,932 A * | 2/1998 | Gillberg et al. | 607/27 |
| 5,800,498 A | 9/1998 | Obino et al. | |
| 5,919,210 A * | 7/1999 | Lurie et al. | 607/3 |
| 6,086,582 A | 7/2000 | Altman et al. | |
| 6,228,049 B1 | 5/2001 | Schroeder et al. | |
| 6,296,630 B1 * | 10/2001 | Altman et al. | 604/508 |
| 6,330,480 B1 * | 12/2001 | Van der Linden et al. | 607/115 |
| 7,133,718 B2 | 11/2006 | Bakken et al. | |
| 7,142,911 B2 | 11/2006 | Boileau et al. | |
| 2002/0188327 A1 * | 12/2002 | Struble | 607/9 |
| 2003/0036773 A1 * | 2/2003 | Whitehurst et al. | 607/3 |
| 2003/0109902 A1 | 6/2003 | Girouard | |
| 2003/0144701 A1 * | 7/2003 | Mehra et al. | 607/17 |
| 2004/0093034 A1 | 5/2004 | Girouard et al. | |
| 2005/0010256 A1 * | 1/2005 | Scharf | 607/9 |

FOREIGN PATENT DOCUMENTS

| | | |
|---|---|---|
| EP | 1 491 234 | 12/2004 |
| EP | 1491234 A | 12/2004 |
| WO | WO 01/34088 A2 | 5/2001 |
| WO | WO0134088 A2 | 5/2001 |
| WO | WO 2004/033036 A2 | 4/2004 |
| WO | WO2004033036 A2 | 4/2004 |
| WO | WO 2004/093969 A1 | 11/2004 |
| WO | WO2004093969 A | 11/2004 |
| WO | WO 2005/084751 A2 | 9/2005 |
| WO | WO2005084751 A2 | 9/2005 |

* cited by examiner

*Primary Examiner* — Nicholas Lucchesi
*Assistant Examiner* — Weng Lee
(74) *Attorney, Agent, or Firm* — Carol F. Barry (57) ABSTRACT

Control of conduction through a heart is described. A lead with a proximal end and a distal end is provided. The distal end of the lead is inserted into a target area. An agent is delivered through the lead to the target area. Delivery of the agent is monitored via a closed loop feedback system.

13 Claims, 14 Drawing Sheets

METHOD AND APPARATUS TO CONTROL CONDUCTION THROUGH THE HEART TO TREAT CARDIAC CONDITIONS

RELATED APPLICATION

This application is related to, and claims the benefit of, provisionally-filed U.S. Patent Application Ser. No. 60/464,767 filed Apr. 23, 2003, and U.S. patent application Ser. No. 10/798,613 filed Mar. 11, 2004 entitled "System for the Delivery of a Biologic Therapy with Device Monitoring and Back-Up", which are incorporated herein by reference in their entirety. This application is also related to, and claims the benefit of, provisionally-filed U.S. Patent Application Ser. No. 60/684,658, filed May 26, 2005.

FIELD OF THE INVENTION

The present invention relates generally to cardiovascular therapies and, more particularly, to control of conduction through the heart.

BACKGROUND OF THE INVENTION

Cardiac conditions such as supraventricular arrhythmias (SVA) or chronic heart block are treated with device therapies, drug therapies, or a combination thereof. Device therapies typically involve implantable medical devices (IMDs). IMDs are effective except with some patients that experience SVA or chronic heart block. One such example relates to implantable pulse generators (IPGs) or implantable cardioverter-defibrillators (ICDs) that deliver electrical stimulation to the vagal nerve plexes located in the heart. Stimulation of vagal nerve plexes enhances parasympathetic input to the atrioventricular (AV) node and subsequently slows AV nodal conduction and ventricular rate. While this therapy operates acutely, tachyphylaxis may occur. Tachyphylaxis is a rapidly decreasing response to a drug or physiologically active agent after administration of a few doses. Additionally, vagal stimulation may induce atrial arrhythmias.

Combined device and drug therapies are costly. One such therapy relates to ventricular rate sensors of an IMD that rely on a sensor-based algorithm to regulate the delivery of drugs. In this case, drugs are typically taken orally on a daily basis regardless of the existence of atrial fibrillation (AF) or inadequate ventricular rate in a heart. A daily dosage is problematic for some patients. For example, some patients are excessively bradycardiac while in sinus rhythm and experience an elevated ventricular rate in AF. To address this problem, a pacemaker is implanted to detect "drug induced brady" conditions and to control the rate of drug delivery. Pacemakers increase patients' costs.

Drug therapies also have drawbacks. Drugs are delivered through systemic circulation of a patient. Examples of systemic drug delivery include oral, intravenous, subcutaneous, or transdermal delivery methods. Since systemic drug delivery introduces drugs to all organs and tissue, non-targeted organs or tissue may exhibit drug toxicity. Drug toxicity concerns limit the dosage that is administered to a patient. Limiting a dosage may reduce the effectiveness of the drug. Systemic drug delivery may also cause side effects in the patient, which reduces tolerability or effectiveness of drugs. For example, drugs that slow down AV nodal conduction may cause side effects such as sinus bradycardia, congestive heart failure, fatigue, or constipation.

Some gene therapies claim to chronically transfect AV nodal tissue with specific genes to control conduction rate through the AV node. However, it is unclear whether these gene therapies adequately control titration of an agent to achieve therapeutic goals. Consequently, gene therapy may result in uncontrollable or inadequate AV nodal rate. It is therefore desirable to have therapies that overcome the limitations described above.

BRIEF DESCRIPTION OF THE DRAWINGS

The present invention will become more fully understood from the detailed description and the accompanying drawings, wherein.

DETAILED DESCRIPTION OF THE EMBODIMENTS

The following description of embodiments is merely exemplary in nature and is in no way intended to limit the invention, its application, or uses. For purposes of clarity, similar reference numbers are used in the drawings to identify similar elements.

The present invention is directed to control of conduction through a heart. This is accomplished, in part, by monitoring delivery of an agent (e.g. drug, biologic, drug/biologic, etc.) to a target area through a closed loop feedback system. Closed loop feedback systems typically relate to implantable medical devices (IMDs). An IMD includes a first and a second lead. The distal end of the first lead is inserted into or around the target area (e.g. atrialventricular (AV) nodal area etc.). The first lead then delivers the agent to the target area. The IMD monitors the electrical response from the heart by accessing data via an electrode at a distal end of a second lead. Adjustments are made to the amount of agent delivered based upon the sensed electrical response from the heart by accessing data. In this manner, a patient's ventricular rate is maintained at an optimal level.

A variety of cardiovascular conditions are treated through control of AV conduction time. For example, the present invention treats paroxysmal chronic supraventricular arrhythmias (i.e. atrial fibrillation, atrial flutter, atrial tachycardia, supraventricular tachycardia). Additionally, chronic heart block (i.e. chronic atrial fibrillation (AF) conditions, chronic AV block conditions) is also treated through the control of the ventricular rate or atrialventricular conduction time. Episodic periods of AF with fast ventricular response are also managed. Furthermore, the present invention improves the treatment and management of atrial bradyarrhythmias.

The present invention also improves treatment of cardiovascular conditions. For example, drug dosages are reduced by five to twenty fold. Additionally, low or undetectable systemic plasma concentrations are obtained. Elimination or diminution is achieved for non-cardiac and cardiac side effects (e.g. ventricular proarrhythmia etc.). Non-orally bio-available drugs can be administered. Greater efficacy or duration of action is obtained. Episodic drug delivery decreases the risk for drug toxicity and complication. Episodic delivery also increases the time periods between drug replacement in the implantable drug delivery arrhythmia management system. A synergistic effect may be obtained in combination with electrical stimulation therapies.

Figure 1:
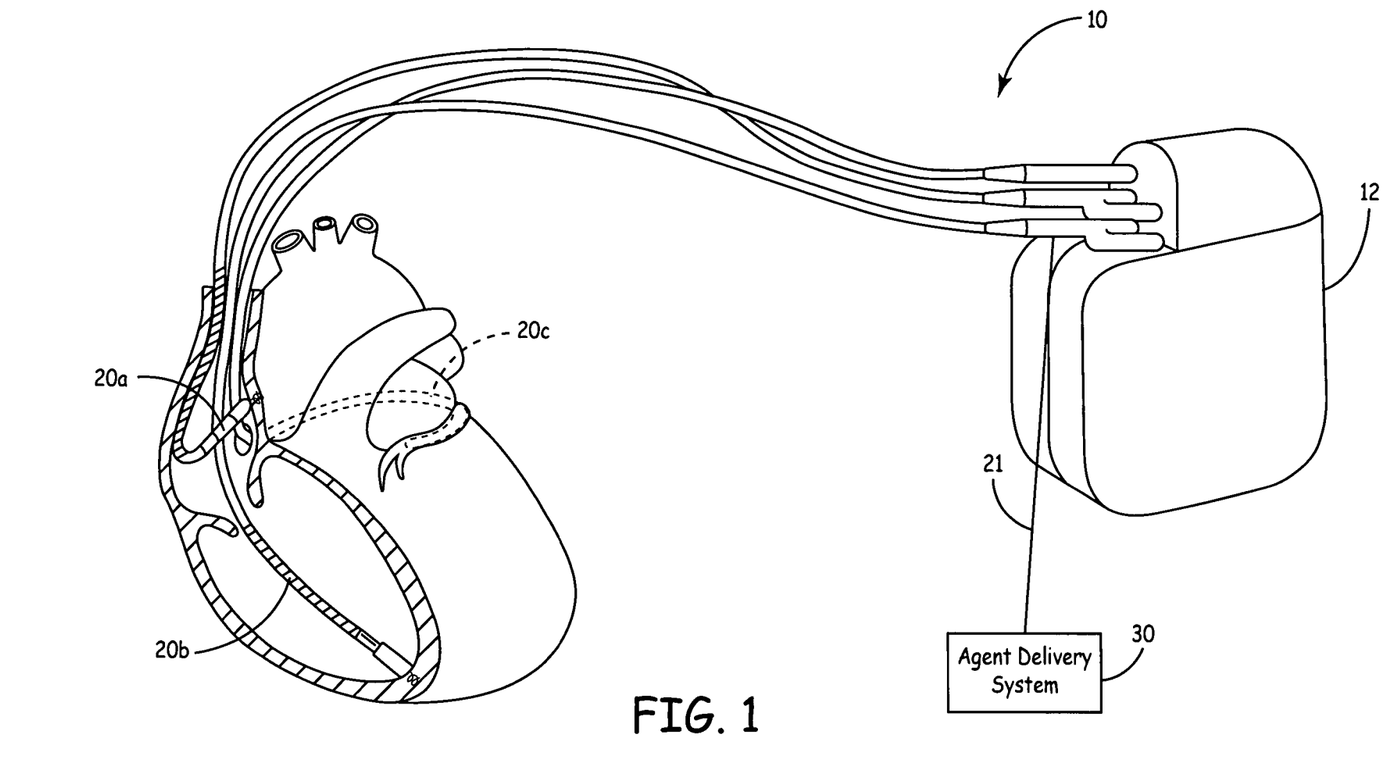
FIG. 1 is a block diagram of an exemplary system to control conduction through a heart.

FIG. 1 depicts a block diagram of system 10 that treats cardiac conditions (e.g. supraventricular arrhythmias, chronic heart block etc.) by monitoring the effectiveness of an agent delivered to myocardial tissue. System 10 includes IMD 12, one or more leads 20a-20c, and agent reservoir 30. A detailed example of an IMD 12 may be seen with respect to a U.S. patent application Ser. No. 10/465,351 filed on Jun. 19, 2003, and assigned to the assignee of the present invention, the disclosure, in relevant part, is incorporated by reference. Exemplary IMDs 12 include an IPG to provide a pacing function, an ICD to provide shocks, a monitoring implant to record various cardiac performance characteristics, or a device that combines these functions.

Leads 20a-20c, which extend from IMD 12, are inserted into or around the myocardial tissue. For example, distal end of lead 20a is in the right atrium, distal end of lead 20b is in the right ventricle, and distal end of lead 20c is in or in close proximity to the AV node. Leads 20a-20c include electrodes to sense data related to cardiovascular variables or parameters. Lead 20c also includes a delivery line (not shown) that allows delivery of the agent to the myocardial tissue. An agent delivery system 30, coupled to lead 20c via conductive line 21, contains and pumps the desired agent (e.g. drug, biologic agent, drug/biologic agent, genetic material etc.) to the myocardial tissue. Line 21 is a coaxial line that includes a conductive line (e.g. wire) and an agent delivery line (not shown).

Figure 2:
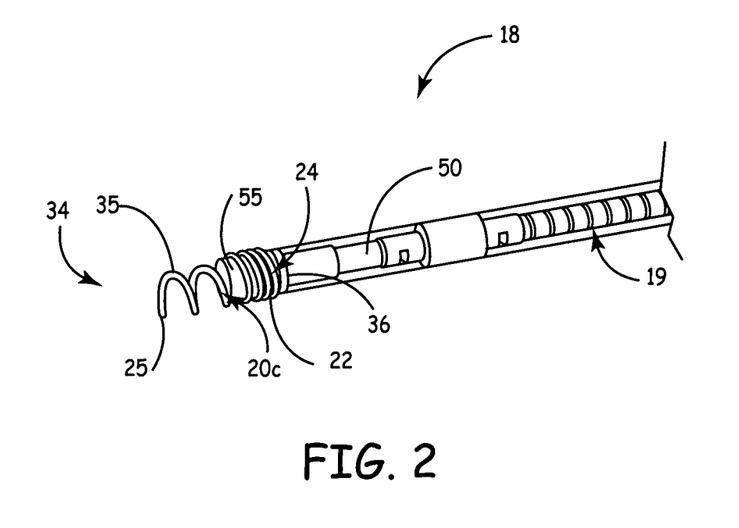
FIG. 2 is a partial perspective view of an exemplary medical device that delivers therapeutic agent to myocardial tissue of a patient.

An exemplary catheter 18 to deliver therapeutic agent to tissue is depicted in FIG. 2. Catheter 18 includes a catheter body 19, lead 20c and a fluid container 50. Lead 20c comprises a lead body 22, one or more electrodes 24, and an anchoring mechanism 34. Lead body 22 has a proximal end 35, a distal end 36, and a lumen therebetween. Anchoring mechanism 34 (e.g. a fixed screw etc.), disposed near distal tip 25 of lead 20c, is configured to secure lead 20c to the myocardial tissue (e.g. AV nodal tissue etc.). Ideally, lead 20c is affixed in or around the triangle of Koch of the myocardial tissue. Fluid container 50 interconnects agent delivery system 30 with the myocardial tissue. Fluid container 50 is guided through lead 20c and is either removed after the procedure or left in place. Distal tip 55 of fluid container 50 either contacts the myocardial tissue or is forced into the myocardial tissue.

System 10 operates as a closed loop feedback system. For example, IMD 12 signals agent delivery system 30 over line 21 to deliver an agent to myocardial tissue. Exemplary agents include calcium channel antagonists, beta-adrenergic antagonists, digitalis-derived drugs, purinergic agents (e.g. adenosine compound, etc.), parasympathetic agents, (e.g. acetylcholine-like compounds, etc.), local anesthetics, adrenergic agonists or other suitable material. In response to signals from IMD 12, agent delivery system 30 pumps agent via a pump (not shown) through lead 20c. The agent is delivered through the fluid container 50 and into or onto the myocardial tissue. The agent regulates AV nodal conduction. For example, the agent controls the speed at which a depolarization wavefront passes from the atrium to the ventricule. In the case of supraventricular tachycardias (SVT), the speed of the depolarization wavefront is decreased. In contrast, the speed of the depolarization wavefront is increased for AV nodal block. Sensed data is then transmitted over one or more leads 20a-20c via their respective electrodes 24 to IMD 12. Based upon the sensed data, IMD 12 then determines whether an adjustment of the agent dosage is required. If an adjustment is required, IMD 12 signals agent delivery system 30 to increase, decrease, or stop agent delivery.

Figure 3:
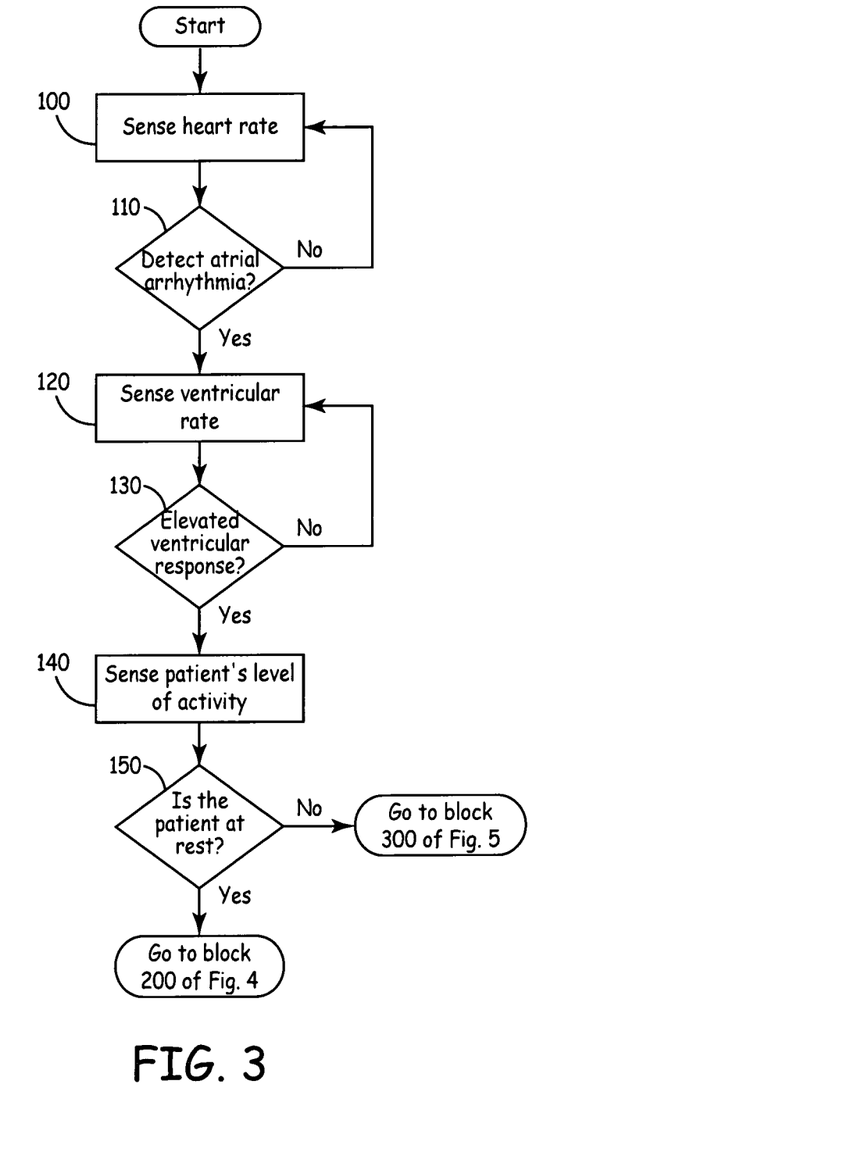
FIG. 3 is a flow diagram of a method to detect cardiac conditions.

FIGS. 3 through 6A-6B generally depict an embodiment to monitor the effect of an agent on myocardial tissue and then, if necessary, adjust the agent dosage. These operations are embodied in computer instructions that are stored in memory (e.g. RAM) and executed on the microprocessor of IMD 12. FIG. 3 specifically relates to monitoring for cardiac conditions. At operation 100, a patient's heart rate is sensed through the electrode(s) of one or more leads 20a-20c. At block 110, a determination is made as to whether an arrhythmia is occurring. If arrhythmia is not detected, system 10 continues to sense data related to the heart rate at block 100. Alternatively, if an arrhythmia is detected, the ventricular rate is sensed by one or more of electrodes of leads 20a-20c at block 120. At block 130, a determination is made as to whether an elevated ventricular response is occurring. An undetected elevated ventricular response causes system 10 to return to block 120 to continue to sense data related to ventricular rate. If an elevated ventricular response is detected, the patient's level of activity is sensed at block 140. At block 150, a determination is made as to whether the patient is at rest. If the patient is at rest, the operation goes to block 300 of FIG. 5. In contrast, if the patient is at rest, the operation goes to block 200 of FIG. 4.

Figure 4:
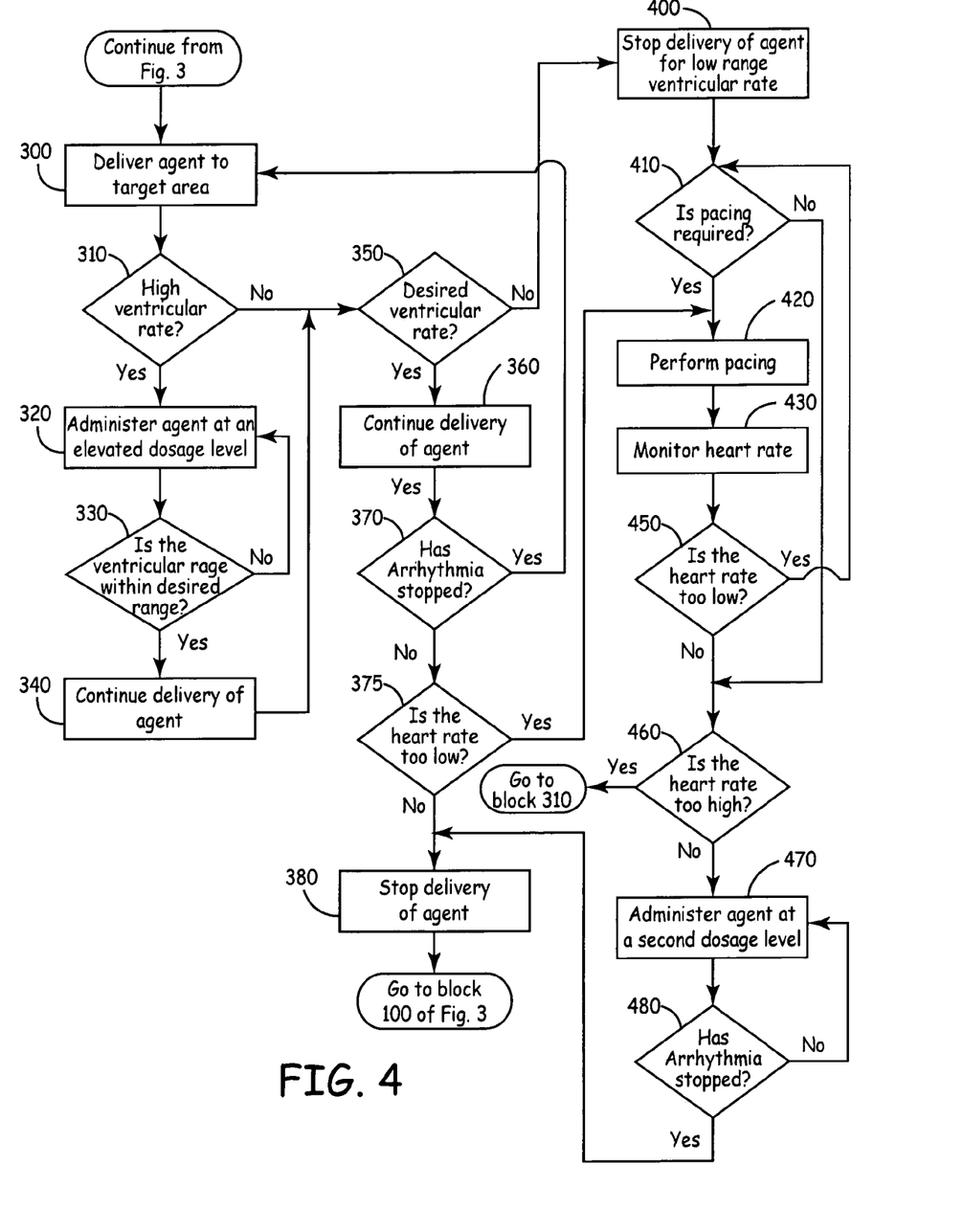
FIG. 4 is a flow diagram of a method to treat cardiac conditions when a patient has low physical activity.

FIG. 4 is a flow diagram depicting a method to treat a patient for cardiovascaular conditions while in an inactive physical state (i.e. rest state). Generally, blocks 300-340 relate to treatment of a high ventricular rate; blocks 350-380 relate to maintaining a desirable ventricular rate; and blocks 410-480 relate to treatment of a low ventricular rate. At block 300, agent delivery to a target area (e.g. AV nodal area, etc.) occurs. At block 310, a determination is made as to whether a high ventricular rate is occurring. Typically, a high ventricular rate is greater than 80 beats per minute (BPM). However, age, pre-existing disease, pre-existing physiological sinus heart rate (if available) and other factors are considered by the physician when programming the ventricular heart rate levels. If high ventricular rate data is sensed from the electrical activity of the myocardial tissue, IMD 12 signals agent delivery system 30 to increase the agent dosage level at block 320. The elevated dosage level is also referred to as a first dosage level. A determination is then made as to whether the ventricular rate is within the desired range after the administration of the first dosage level at block 330. A desired ventricular rate range is typically greater than 60 BPM and less than 80 BPM. If the ventricular rate is not within the desired range after a certain time period, the agent is administered at another elevated dosage level at block 320. For example, if the ventricular rate exceeds 100 bpm for over 5 minutes at rest while a drug is administered at a given dosage X, then dosage X is increased 10-200% until the ventricular rate is within the desired range. Alternatively, if the ventricular rate is determined to be within the desired range, delivery of the agent in its current dosage is continued at block 340.

If it is determined that a high ventricular rate does not exist at block 310, the operation turns to maintenance of a desired ventricular rate. A determination is made as to whether the ventricular rate is within a desired range at block 350. If the ventricular rate is below the desired ventricular rate, delivery of the agent is stopped at block 400. If the ventricular rate is within the desired range, the agent is continuously delivered in its current dosage at block 360. A determination is then made as to whether the arrhythmia has stopped at block 370. If the arrhythmia has ceased, the agent is continuously delivered at its current dosage to the target area at block 300. If not, a determination is made as to whether the heart rate is too low at block 375. If the heart rate is not too low, delivery of the agent is stopped at block 380 and system 10 returns to monitoring cardiovascular conditions at block 100 of FIG. 3. If the heart rate is too low, a pacing operation is implemented at operation 420.

Blocks 400-480 generally relate to treatment of a low ventricular rate. At block 400, delivery of the agent is stopped for low range ventricular rate (e.g. typically less than 60 BPM). At block 410, a determination is made as to whether pacing is required. If pacing is required, pacing is performed at block 420 by one of the leads 20a-20c. At block 430, the heart rate is monitored. At block 450, a determination is made as to whether the heart rate is too low. If the heart rate is too low, the operation makes a determination as to whether pacing is required at block 410. If the heart rate is not too low, a determination is made as to whether the heart rate is too high at block 460. If the heart rate is too high, the operation goes to block 310 to determine whether a high ventricular rate exists. If the heart rate is not too high, the agent is administered at a certain dosage level at block 470. For example, if the heart rate is at 160 bpm during exercise, then the AVN blocker drug such as calcium channel blocker agent (e.g. verapamil etc.) is continuously delivered. A determination is then made at block 480 as to whether the arrhythmia has stopped. If the arrhythmia has stopped, delivery of the agent is stopped at block 380. If the arrhythmia has not stopped, the agent is delivered at a certain dosage level at block 470. This dosage level is referred to as a second dosage level.

Figure 5:
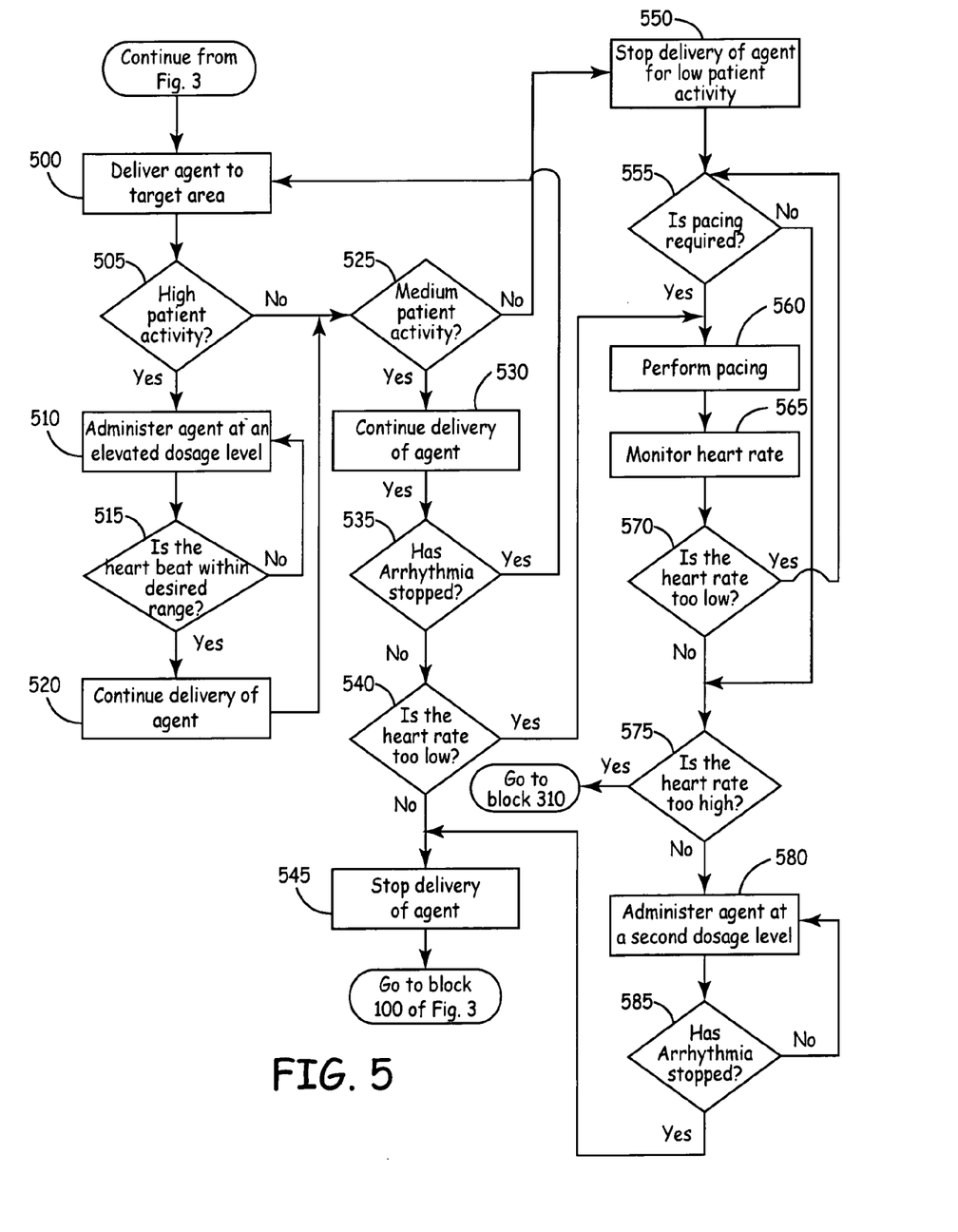
FIG. 5 is a flow diagram of a method to treat cardiac conditions when a patient has increased physical activity.

FIG. 5 is a flow diagram that depicts treatment of a cardiac condition based upon the activity of a patient instead of ventricular rate. At block 500, agent delivery to a target area (e.g. AV nodal area, etc.) occurs. At block 505, a determination is made as to whether a patient exhibits high physical activity. U.S. patent application Ser. No. 10/465,351, incorporated by reference, in relevant part, briefly describes sensors for activity.

Typically, high physical activity is determined by increased activity of these sensors (e.g. motion sensor, etc.). If high physical activity data is sensed from the electrical activity of the myocardial tissue, IMD 12 signals agent delivery system 30 to increase the agent dosage level at block 510. The elevated dosage level is also referred to as a first dosage level. A determination is then made as to whether the patient, who is experiencing high physical activity, nevertheless maintains the heart beat within a desired range after the administration of the first dosage level at block 515. If the heart rate is not within the desired range within a certain time period, the agent is administered at another elevated dosage level at block 510. For example, the patient has a ventricular rate of 180 bpm at a given dosage level X, then this dosage level is increased by 10-200%. Alternatively, if the heart rate is determined to be within the desired range, delivery of the agent in its current dosage is continued at block 520.

If it is determined that a high physical activity does not exist at block 505, the operation turns to medium level of physical activity operations. A determination is made as to whether medium physical activity is occurring at block 525. If the ventricular rate is below the desired ventricular rate, delivery of the agent is stopped at block 550. If medium physical activity is occurring, the agent is continuously delivered in its current dosage at block 530. A determination is then made as to whether the arrhythmia has stopped at block 535. If the arrhythmia has ceased, the agent is continuously delivered at its current dosage to the target area at block 500. If not, a determination is made as to whether the heart rate is too low at block 540. If the heart rate is not too low, delivery of the agent is stopped at block 545 and the system returns to monitoring cardiovascular conditions at block 100 of FIG. 3.

Blocks 550-585 generally relate to treatment of a patient during low physical activity. At block 550, delivery of the agent is stopped for low range ventricular rate (e.g. less than 60 BPM). At block 555, a determination is made as to whether pacing is required. If pacing is required, pacing is performed at block 560 by one of the leads 20a-20c. At block 565, the heart rate is monitored. At block 570, a determination is made as to whether the heart rate is too low. If the heart rate is too low, the operation makes a determination as to whether pacing is required at block 555. If the heart rate is not too low, a determination is made as to whether the heart rate is too high at block 575. If the heart rate is too high, the operation goes to block 505 to determine whether a high physical activity exists. If the heart rate is not too high, the agent is administered at a certain dosage level at block 580. For example, a calcium blocking agent may be delivered if the ventricular heart rate is 160 beats per minute. A determination is then made at block 585 as to whether the arrhythmia has stopped. If the arrhythmia has stopped, delivery of the agent is stopped at block 545. If the arrhythmia has not stopped, the agent is delivered at a certain dosage level at block 580. This dosage level is referred to as a second dosage level.

Figure 6A:
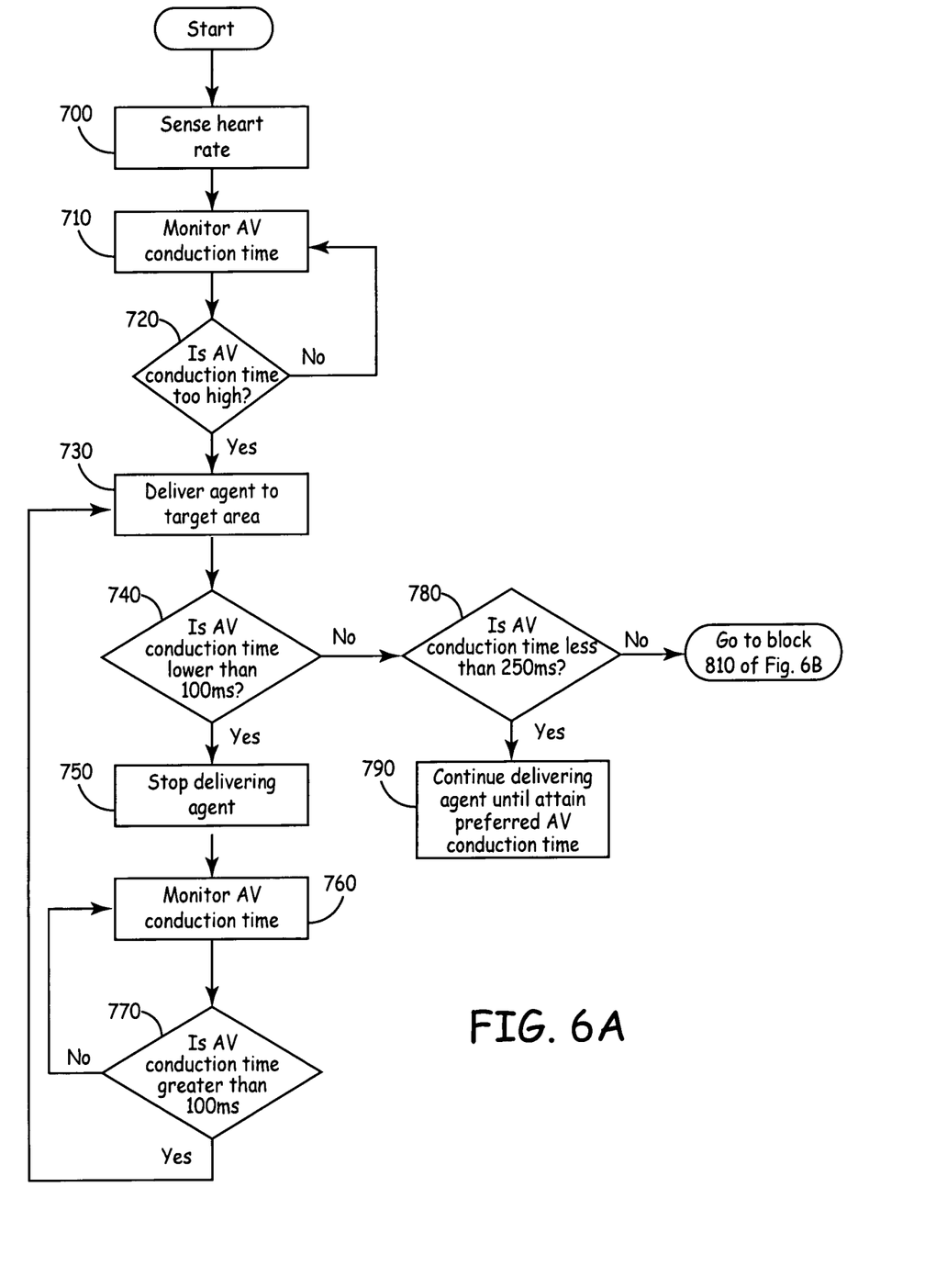
FIGS. 6A-6B are flow diagrams of a method to control atrial ventricular conduction time.
Figure 6B:
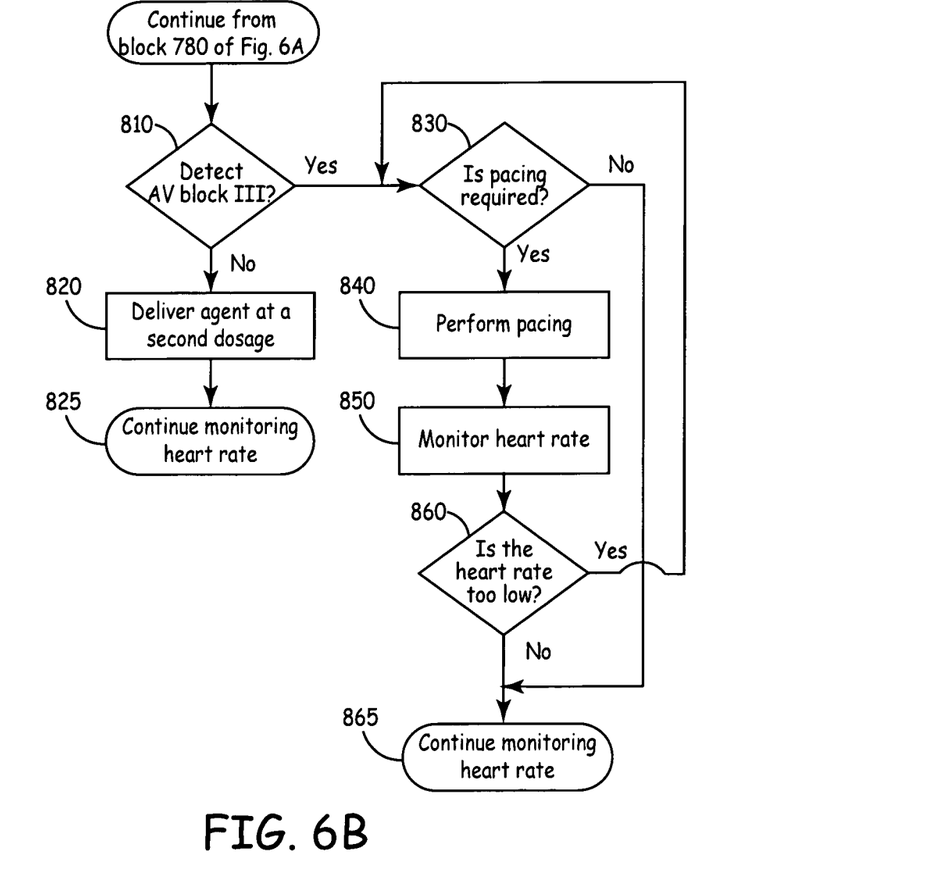

FIGS. 6A and 6B depict operations to control AV conduction time. At block 700, the heart rate is sensed by system 10. At block 710, AV conduction time is monitored. At block 720, a determination is made as to whether AV conduction time too high. If AV conduction time is not too high, the operation loops back to block 710 to monitor AV conduction time. Alternatively, if AV conduction time is too high, agent is delivered to the target area at block 730. At block 740, a determination is made as to whether AV conduction time is lower than 100 microseconds. If AV conduction time is not lower than 100 milliseconds (ms), a determination is then made at block 780 as to whether AV conduction time is less than 250 ms. In contrast, if AV conduction time is lower than 100 ms, agent delivery is stopped at block 750. At block 760, AV conduction time is monitored. At block 770, a determination is made as to whether AV conduction time is greater than 100 ms. If AV conduction time is not greater than 100 ms, system 10 loops back to block 760 to monitor AV conduction time. Alternatively, if AV conduction time is greater than 100 ms, the agent is delivered to the target area at block 730.

Turning now to block 780, a determination is made as to whether AV conduction time is less than 250 ms. If AV conduction time is less than 250 ms, delivery of the agent continues at its current dosage at block 790.

At block 810, a determination is made as to whether AV block III is occurring in the patient. If it is not present, agent delivery continues at a specified dosage at block 820. The heart rate is monitored and appropriate action is taken if a cardiac condition is detected at block 825. Optionally, control of system 10 returns to block 700. In contrast, if AV block III is occurring, a determination is made as to whether pacing is required at block 830. If pacing is required, a pacing operation is implemented at block 840. The patient's heart rate is monitored at block 850. A determination is made as to whether the heart rate is too low at block 860. At block 865, the heart rate is monitored and appropriate action is taken if a cardiac condition is detected. Optionally, control of system 10 returns to block 700.

Figure 7:
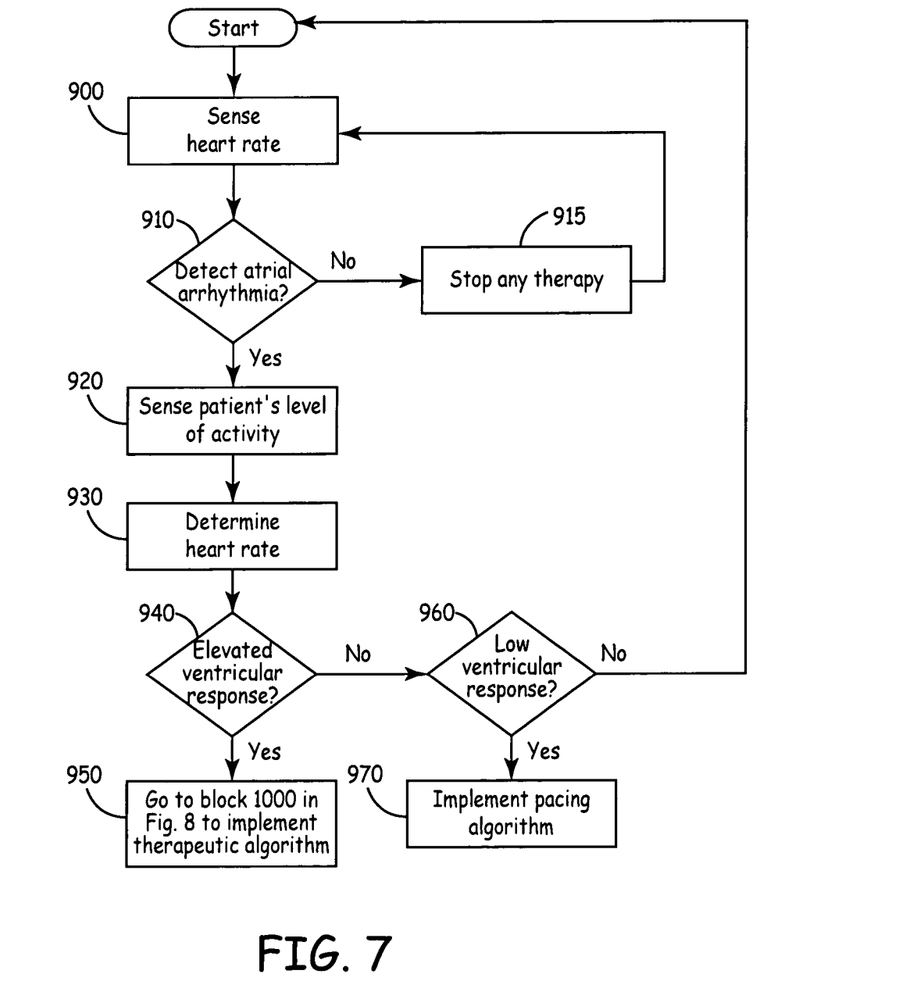
FIG. 7 is a flow diagram of a method to detect cardiac conditions.
Figure 8:
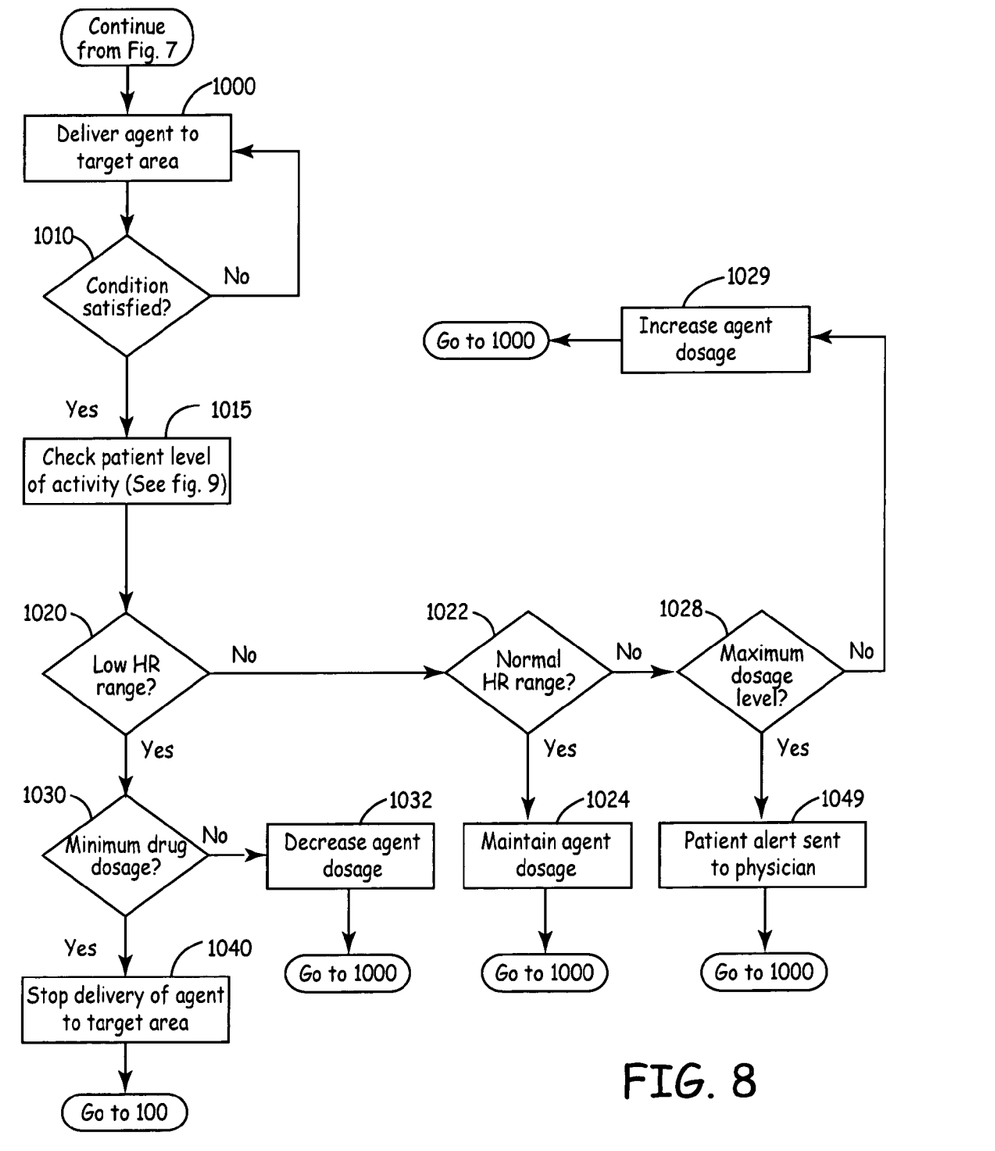
FIG. 8 is a flow diagram of a method to treat cardiac conditions.
Figure 9:
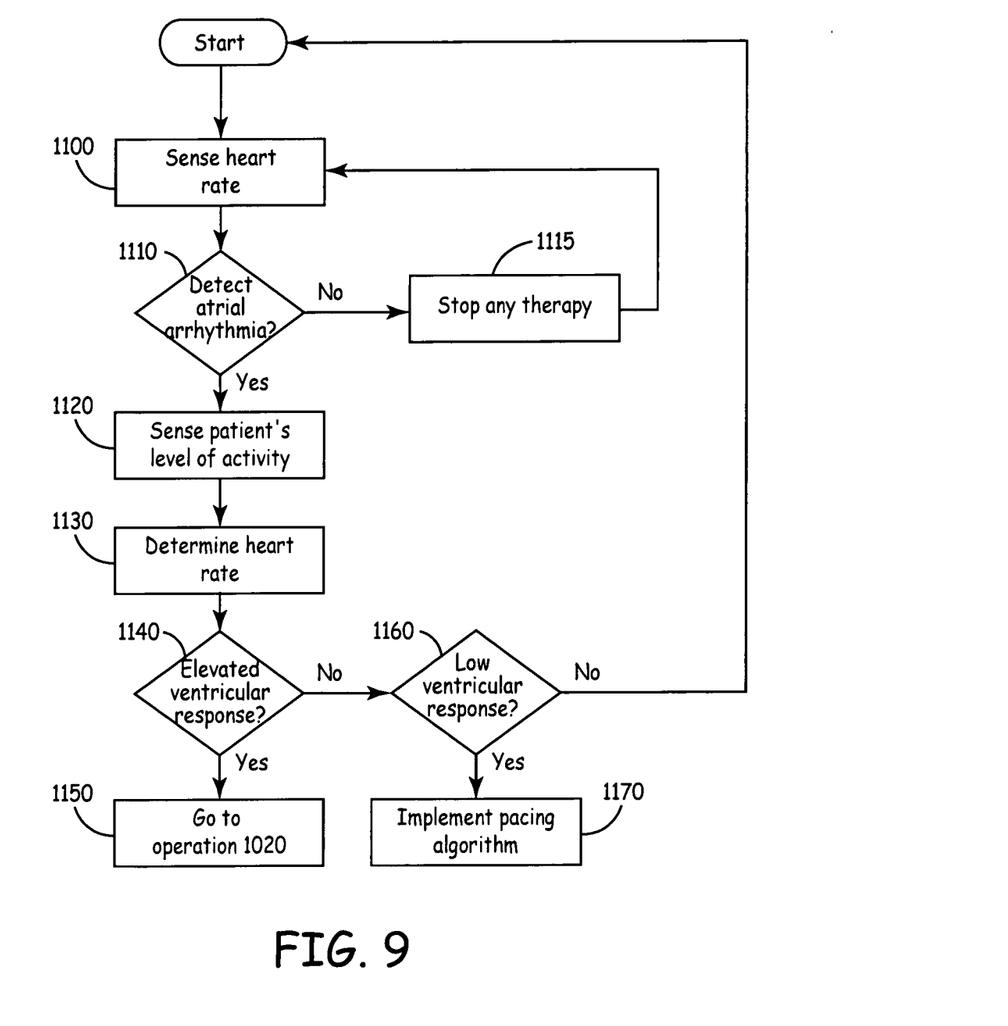
FIG. 9 is a flow diagram of a method to treat cardiac conditions based upon patient activity.

FIGS. 7-9 illustrate another embodiment to control conduction through a heart. FIG. 7 depicts operations that determine whether a therapeutic algorithm or a pacing algorithm are implemented. At block 900, the heart rate of a patient is sensed. At block 910, a determination is made as to whether atrial arrhythmia is detected. If no atrial arrhythmia is detected, any therapy is stopped at operation 915 and the system returns to sensing the heart rate at block 900. If atrial arrhythmia is detected, the patient's level of activity is sensed at block 920. At block 930, the heart rate is determined. At operation 940, a determination is made as to whether an elevated ventricular response is present. If so, the therapeutic algorithm is implemented at operation 950 and the operations in FIG. 8 are then followed. If an elevated ventricular response is not detected, a determination is made as to whether a low ventricular response is present at block 960. If so, a standard pacing algorithm is implemented at operation 970 and the operations of FIG. 9 are implemented. However, if a low ventricular response is not detected, control of the algorithm returns to the start operation.

FIG. 8 is a flow diagram related to administration of a therapeutic agent taking into consideration a patient's level of physical activity. At operation 1000, an agent is delivered to the target area (e.g. triangle of Koch area). At operation 1010, a determination is made as to whether a condition is satisfied. Exemplary conditions include the elapsed time from which the agent was delivered to the target area, variables related to AF, slope of heart rate change, or other suitable conditions. If the condition is not satisfied, control of the operation returns to block 1000 in which the agent continues delivery. In contrast, if the condition is satisfied, the patient's level of activity is checked at block 1015. A determination is then made as to whether a low heart range is present at block 1020. If a low heart range is present, a determination is made as to whether a minimum dosage level is being applied to patient at block 1030. If the minimum dosage level is being used, delivery of the agent at target area is stopped at block 1040 and control of the algorithm returns to block 100. In contrast, if a minimum dosage level is not present, the agent dosage is decreased at operation 1032 to control of system 10 then turns to block 1000.

If a low heart range is not present in the patient, a determination is then made at block 1022 as whether a normal heart range is present. If the normal heart range is occurring, agent dosage is maintained at block 1024 and control of system 10 returns to block 1000. If a normal heart range is not present in the patient, a determination is made as to whether the patient is being administered at maximum agent dosage level at block 1028. If not, agent dosage is increased at block 1029 and control of system 10 returns to block 1000. In comparison, if the patient is at the maximum dosage level, a patient alert is sent to the physician at block 1026 and control of the algorithm returns to block 1000 at operation 1049.

FIG. 9 relates to checking patient's level of activity. At operation 1100, the heart rate of the patient is sensed. At block 1110, a determination is made as to whether atrial arrhythmia is occurring. If not, any applicable therapy is stopped at block 1115 and control of system 10 returns to sensing the heart rate at 1100. If atrial arrhythmia is detected, the patient's level of activity is sensed using an activity sensor at block 1120. A determination is made as to the patient's heart rate at block 1130. At block 1140, a determination is made as to whether an elevated ventricular response is present. At block 1150, if there is an elevated ventricular response, control of the algorithm returns to block 1020. In contrast, if an elevated ventricular response is not present, a determination is made as to whether a low ventricular response is occurring in the patient at block 1160. A standard pacing algorithm is implemented at block 1170 if a low ventricular response is present. In contrast, if the patient lacks a low ventricular response, control of the operation returns to the start of the algorithm.

FIGS. 10A-10D represent in vivo experimental data obtained from anesthetized animals based upon features of the claimed invention. Specifically, this data demonstrates that local drug delivery directly into the AVN region effectively controls ventricular rate during AF without producing systemic effects and toxicity. This study evaluated the effect of locally administered acetylcholine (ACH) on AVN conduction and refractoriness properties during sinus rhythm and AF. Canines (n=7) were anesthetized, and instrumented to assess atrial and ventricular electrophysiology as well as arterial blood pressure. A custom drug delivery catheter was fixed into the AVN region using a combination of standard electrophysiological mapping techniques and image guided therapy via a cardiac navigation system. Its location was confirmed by delivering an ACH test dose and resultant complete, but fully reversible heart block in all 7 animals. As noted from data presented below in Table 1, the duration of AV block administered via direct AVN injection was substantially longer than for intravenous administration of the identical dose.

TABLE 1

AV Block III duration and overall AV Block duration for direct AVN Bolus injection vs. Intravenous Bolus injection.

| | Direct AVN Bolus (n = 6) | Intravenous Bolus (n = 5) |
|---|---|---|
| Overall AV Block duration* (min) | 41.19 ± 27.14 | 0.31 ± 0.43 |
| AV Block III duration (min) | 12.30 ± 4.72 | 0.00 ± 0.00 |

*Duration of AV block I, II and III

Figure 10A:
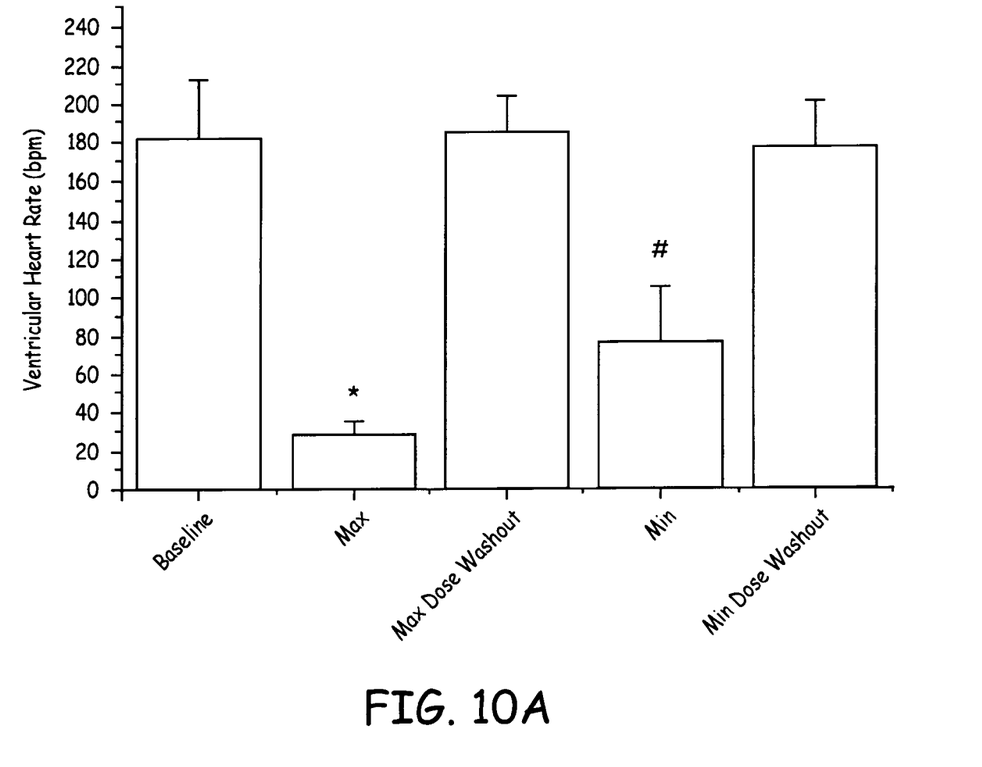
FIG. 10A is a bar diagram in which ventricular rate is controlled.
Figure 10B:
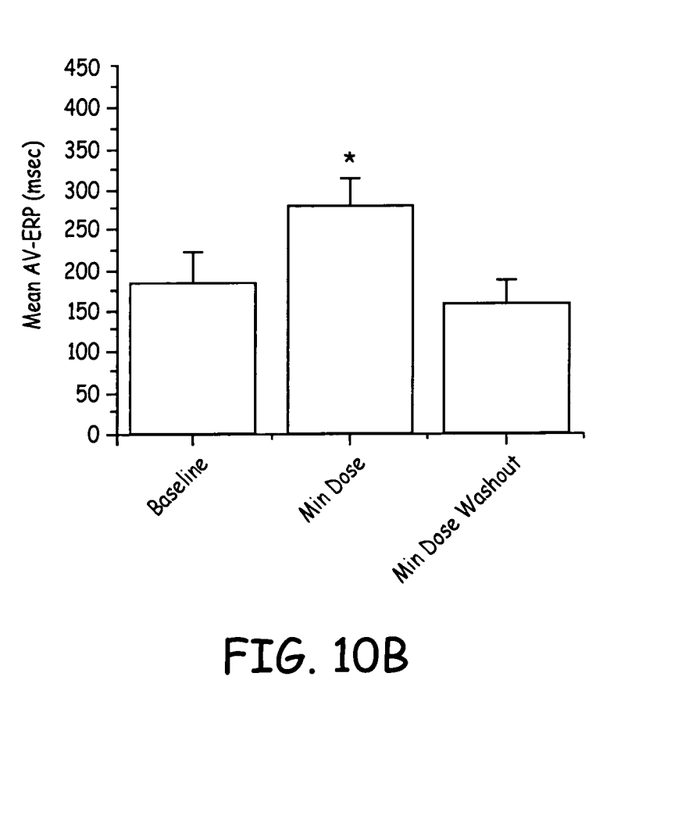
FIG. 10B is a electrocardiogram in which ventricular rate is controlled.
Figure 10C:
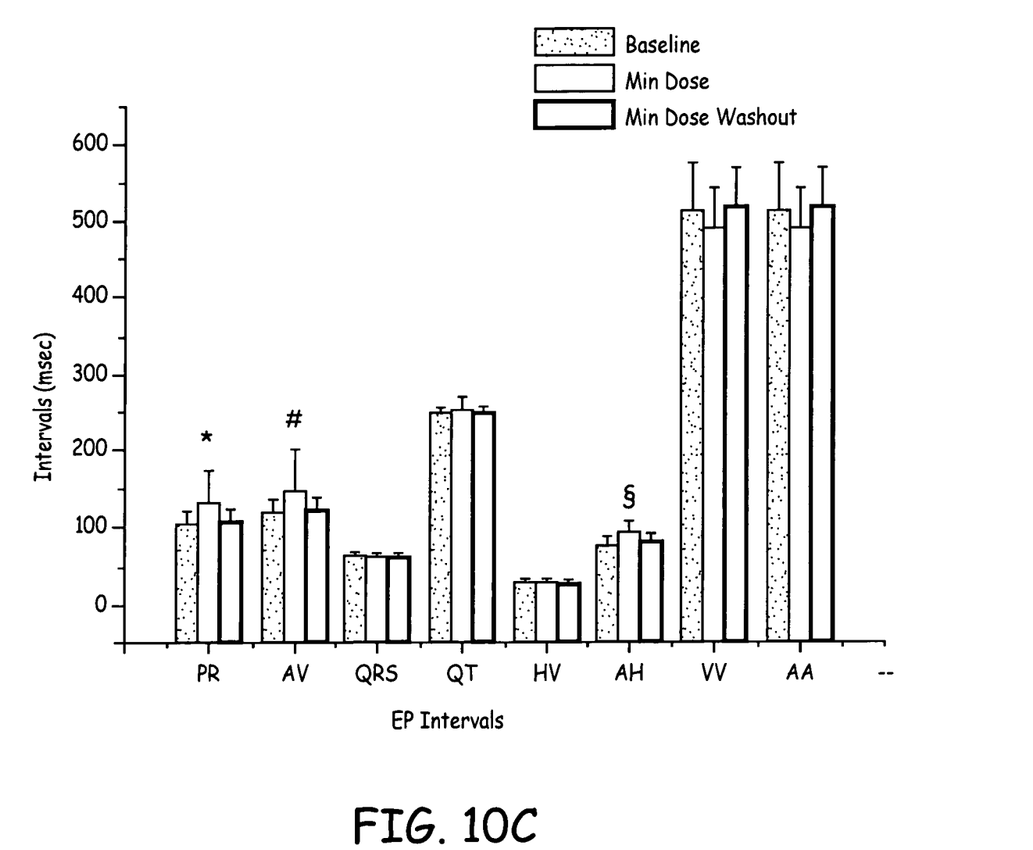
FIG. 10C is a block diagram of FIG. 10B in which ventricular rate is controlled.
Figure 10D:
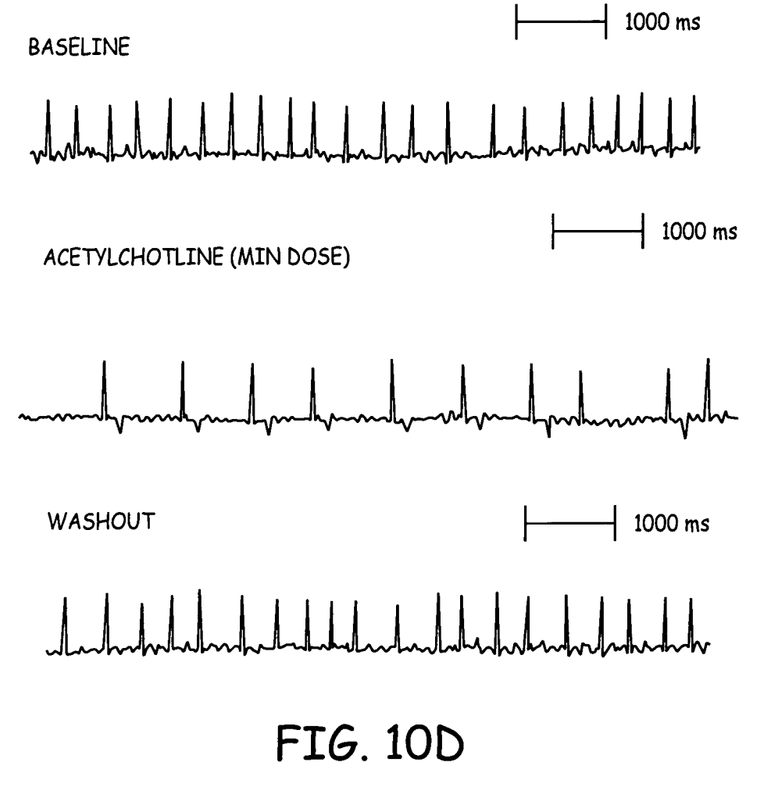
FIG. 10D is a bar diagram of reversible increase of AH and AV intervals during continuous administration of an agent.

Subsequently, incremental doses of ACH starting at 10 ug/min were infused into the AVN until complete atrioventricular heart block (AVB) was observed. ACH produced AVB in a dose dependent manner. During electrically induced AF, the ventricular rates decreased from 182±32 to 77±28 beats per minutes (bpm) (acetylcholine dosage inducing first degree AVB; p<0.05) and to 28±8 bpm (third degree AVB; p<0.05) (FIG. 10A). Raw data obtained during electrically induced AF are shown in FIG. 10B during and without drug administration. At the first degree AVB dose, AVN effective refractory period (ERP) at a pacing cycle length of 400 milliseconds (msec) increased from 186±37 msec to 282±33 msec (p=0.06), and Wenckebach cycle length from 271±29 msec to 378±58 msec (p<0.05) (FIG. 10C). In addition, ACH dose producing first AVB prolonged AV, PR and AH intervals, whereas PP intervals, HV intervals and blood pressure remained unchanged, demonstrating a local effect (FIG. 10D). Observed effects were fully reversible within 20 minutes after stopping ACH infusion. From this in vivo data, local ACH delivery into the AVN region successfully increased AVN refractoriness and significantly decreased ventricular rate response during electrically induced AF in a dose related fashion. These effects occurred without significant systemic effects and were rapidly reversible within minutes. This may represent a novel drug delivery therapy whereby direct AVN drug delivery is monitored and controlled to maintain an optimal ventricular rate during AF events.

The present invention has numerous applications. For example, while the figures relate to AF, other types of cardiac conditions may be treated by this process. For example, AV block may rely on the embodiment presented in FIGS. 7-9. To illustrate, blocks 1020 and 1028 may be switched with each other. Additionally, the blocks that describe "atrial arrhythmia" are switched to AV block. The rest of the blocks remain unchanged. The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A method of treating atrial fibrillation in a patient, the method comprising:
    delivering a catheter to AV nodal tissue of the patient;
    fixating the catheter to the AV nodal tissue;
    determining an occurrence of atrial fibrillation;
    delivering a calcium channel blocker agent into the AV nodal tissue to increase AV nodal tissue refractoriness and decrease ventricular rate upon determining the occurrence of atrial fibrillation;
    monitoring an electrical response by the heart to the calcium channel blocker agent via a closed loop system, wherein the electrical response comprises at least one of a parameter representative of AV nodal refractoriness and a parameter representative of ventricular rate, wherein the electrical response comprises at least AV conduction time; and
    adjusting quantity of the delivered calcium channel blocker agent using the closed loop system based on at least one of the parameter representative of AV nodal refractoriness and the parameter representative of ventricular rate, wherein adjusting quantity of the delivered calcium channel blocker agent using the closed loop system is based at least on AV conduction time.

2. A method of treating atrial fibrillation in a patient, the method comprising:
    delivering a catheter to AV nodal tissue of the patient;
    fixating the catheter to the AV nodal tissue;
    determining an occurrence of atrial fibrillation;
    delivering a calcium channel blocker agent into the AV nodal tissue to increase AV nodal tissue refractoriness and decrease ventricular rate upon determining the occurrence of atrial fibrillation;
    monitoring an electrical response by the heart to the calcium channel blocker agent via a closed loop system, wherein the electrical response comprises at least AV conduction time; and
    adjusting quantity of the delivered calcium channel blocker agent using the closed loop system based at least on AV conduction time,
    wherein the AV nodal tissue is within a triangle of Koch.

3. The method of claim 1 further comprising ceasing delivery of the calcium channel blocker agent responsive to determining AV conduction time is lower than 100 ms.

4. The method of claim 3 further comprising:
    determining AV conduction time is higher than 100 ms; and
    determining AV conduction time is less than 250 ms.

5. The method of claim 4 further comprising continuing delivery of the calcium channel blocker agent responsive to determining AV conduction time is less than 250 ms.

6. The method of claim 1 further comprising determining AV conduction time is higher than 100 ms.

7. The method of claim 6 further comprising determining AV conduction time is higher than 250 ms.

8. The method of claim 7 further comprising:
    determining AV block III is present in the patient; and
    delivering the calcium channel blocker agent at a second dosage.

9. The method of claim 7 further comprising determining pacing is required.

10. The method of claim 1 wherein the catheter includes a fluid container for holding the calcium channel blocker agent, the fluid container having a distal tip for delivering the calcium channel blocker agent.

11. A method of treating atrial fibrillation in a patient, the method comprising:
    delivering a catheter to AV nodal tissue of the patient, the catheter having a distal end;
    penetrating the AV nodal tissue with the distal end of the catheter;
    delivering a calcium channel blocker agent into the AV nodal tissue through the catheter to increase AV nodal tissue refractoriness and decrease ventricular rate;
    monitoring an electrical response by the heart to the calcium channel blocker agent via a closed loop system, wherein the electrical response comprises at least AV conduction time; and
    adjusting quantity of the delivered calcium channel blocker agent using the closed loop system based at least on AV conduction time.

12. A method of treating atrial fibrillation in a patient, the method comprising:
    delivering a catheter to AV nodal tissue of the patient, the catheter having a distal end;
    penetrating the AV nodal tissue with the distal end of the catheter;
    delivering an agent into the AV nodal tissue through the catheter to increase AV nodal tissue refractoriness and decrease ventricular rate;
    monitoring an electrical response by the heart to the agent via a closed loop system, wherein the electrical response comprises at least AV conduction time; and
    adjusting quantity of the delivered agent using the closed loop system based at least on AV conduction time.

13. A method of treating atrial fibrillation in a patient, the method comprising:
    delivering a catheter to a triangle of Koch of the patient;
    penetrating the triangle of Koch with a distal end of the catheter;
    delivering a calcium channel blocker agent through the catheter into the triangle of Koch to increase AV nodal tissue refractoriness and decrease ventricular rate; and
    monitoring an electrical response by the heart to the calcium channel blocker agent via a closed loop system, wherein the electrical response comprises at least AV conduction time, and
    adjusting quantity of the delivered calcium channel blocker agent using the closed loop system based at least on AV conduction time.

* * * * *